United States Patent [19]

Kanagawa et al.

[11] 4,107,981
[45] Aug. 22, 1978

[54] METHOD OF ESTIMATING GROUND PRESSURE

[75] Inventors: Tadashi Kanagawa, Kashiwa; Hiroyasu Nakasa, Tokyo, both of Japan

[73] Assignee: Central Research Institute of Electric Power Industry, Tokyo, Japan

[21] Appl. No.: 811,598

[22] Filed: Jun. 30, 1977

[30] Foreign Application Priority Data

Sep. 22, 1976 [JP] Japan .................................. 51-113938

[51] Int. Cl.² ............................................. G01N 3/06
[52] U.S. Cl. ..................................... 73/88 E; 73/587
[58] Field of Search ....................... 73/88 E, 587, 88.3, 73/71.4

[56] References Cited

U.S. PATENT DOCUMENTS

| | | | |
|---|---|---|---|
| 3,858,439 | 1/1975 | Nakamura | 73/587 |
| 3,865,201 | 2/1975 | Haden | 73/151 |
| 3,875,381 | 4/1975 | Wingfield et al. | 73/587 |
| 4,006,625 | 2/1977 | Davis | 73/587 |

*Primary Examiner*—Anthony V. Ciarlante
*Attorney, Agent, or Firm*—Wenderoth, Lind & Ponack

[57] ABSTRACT

A method of estimating ground pressure in rock samples by making use of the Kaiser effect of acoustic emission. The method comprises the steps of applying load to a rock sample, increasing the load and counting the summation of the acoustic emissions produced from the interior of the rock sample. The ground pressure is determined from the magnitude and direction of hysteretic maximum stress in the ground where the rock sample was extracted.

5 Claims, 3 Drawing Figures

METHOD OF ESTIMATING GROUND PRESSURE

BACKGROUND AND SUMMARY OF THE INVENTION

This invention relates to a method of estimating geo-stress or ground pressure making use of the Kaiser effect of acoustic emission and, more particularly, a method of estimating ground pressure by applying load to each rock sample extracted from the ground, counting the number of emissions of sound during the application of the load and determining the ground pressure from the magnitude and direction of residual stress in the ground where the rock sample was extracted.

When removing rocky ground, cutting a tunnel, cutting a level or a shaft for extracting underground resources, or building a large-scale underground structure for an atomic power station or the like, it is important from the standpoint of the work plan to grasp the stress state of the relevant ground beforehand. The stability of the ground after the work is completed is greatly influenced by the magnitude and direction of the ground pressure, and there are many cases leading to, for instance, collapse of excavated surface, shift or collapse of tunnel side walls, rock burst and so forth.

There are several conventional methods of measuring the actual geo-stress, the ground pressure state under the prevailing condition of the ground. In any of these methods, however, some gauge or measuring instrument is buried in the ground for measurement, thus requiring considerable time and expense in addition to the fact that it is difficult to obtain a sufficiently great amount of data. The so-called over-coring method is a typical conventional method. In the over-coring method, a strain gauge is buried in a bore of a small diameter (of about 60 mm), and thereafter a concentric over-coring bore of a large diameter (of about 200 mm) is bored for estimating the ground pressure by measuring the strain in the state with stress released. This method requires a period of about a month and the afore-mentioned large-diameter boring for each point of measurement. Therefore, it sometimes happens that measurement is impossible or it is difficult to obtain many samples depending upon the site.

Meanwhile, a phenomenon commonly termed Kaiser effect is known in the acoustic emission test method. The Kaiser effect occurs when that the material structure is steady and stable and is less subject to acoustic emission up to the prior hysteretic maximum stress, but the structure becomes liable to microscopic destruction due to increased acoustic emission when it receives a stress in excess of the aforementioned stress. This effect is utilized for testing the presence or absence of the reduction of the structural quality of metal structures, such as pressure containers or pipe lines, during their period of operation, but in the field of testing of metallic materials the directivity of the Kaiser effect is not yet clear yet.

This invention is predicated in the finding that rocks also present the Kaiser effect and that directivity is present in that effect.

Accordingly, an object of the present invention is to provide a method of estimating ground pressure, which allows a simple, ready and economic estimation of the ground pressure.

Another object of the present invention is to provide a method of estimating ground pressure, without having to bury a strain gauge or like instrument in the ground.

BRIEF DESCRIPTION OF THE DRAWINGS

Other objects and features of the present invention will become apparent from the detailed description of the peferred embodiment thereof, which will be read with reference to the accompanying drawings.

DESCRIPTION OF THE DRAWINGS

Figure 1:
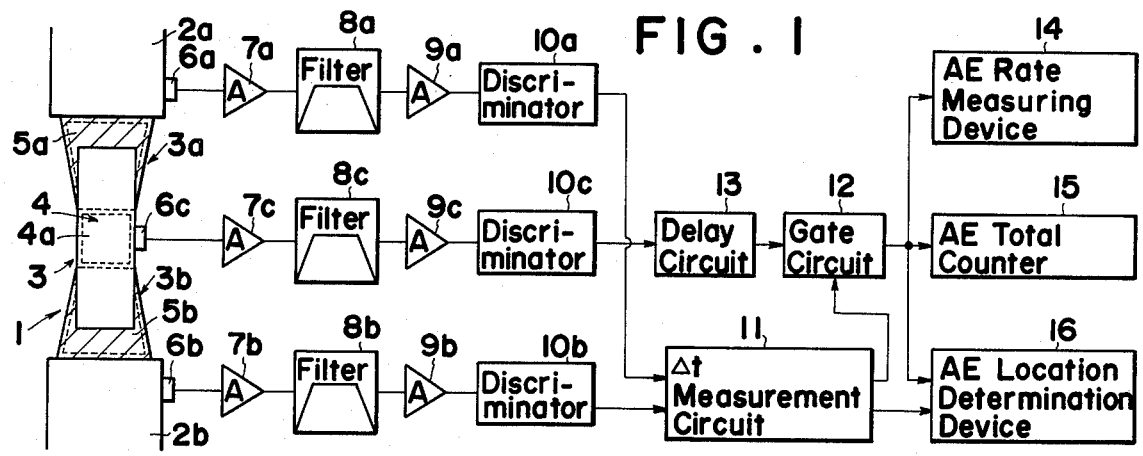
Figure 2:
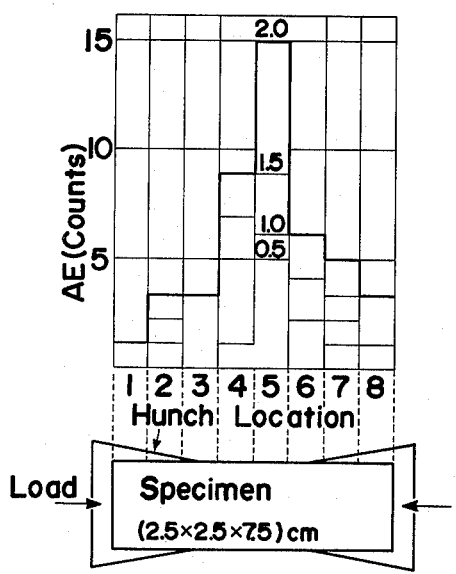

FIG. 1 is a schematic diagram showing a measurement system used in accordance with the present invention;

FIG. 2 is a graph showing an example of the result of location estimation; and

Figure 3:
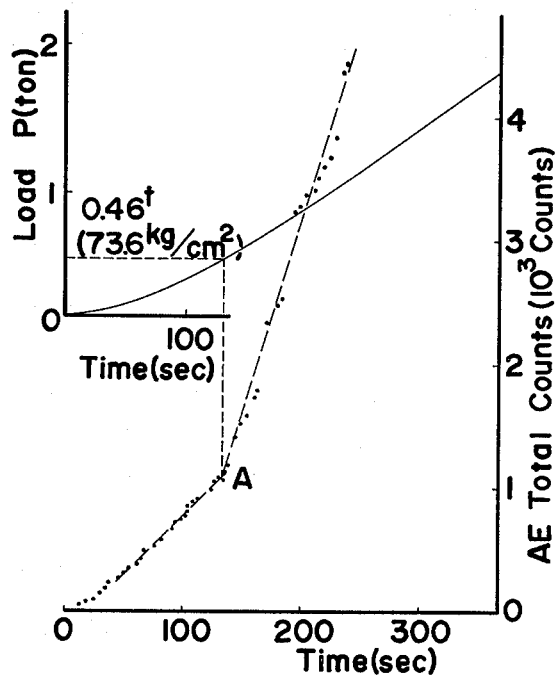

FIG. 3 is a graph showing an example of the results of measurement.

DETAILED DESCRIPTION OF THE INVENTION

First, rock pieces are extracted from a predetermined position in the ground. This extraction may be done by any suitable method, for instance boring from the ground surface or from the interior of a level or block sampling from a prospecting level. In order to understand the three-dimensional stress state of the ground, it is necessary to know stresses in three perpendicular directions, and to this end it is necessary to obtain at least rock samples capable of measurement of stress in these three directions. Where large-size rock pieces can be extracted in the aforementioned rock sampling, it is convenient to permit rock samples in a plurality of different orientations to be extracted while making definite their direction in the ground. On the other hand, where only small-size rock pieces can be extracted, as in the small diameter boring, the boring may be made a plurality of times by setting the direction of the bore into the required particular direction.

The rock samples obtained in this way, are tested by putting them into a testing device as shown in FIG. 1. FIG. 1 shows an example of the testing device, which mainly comprises a loading device and a signal processing device. The loading device 1 is a uni-axial compression tester, in which a sample 3 is interposed between loading plates 2a and 2b. The sample 3 is a prismatic rock body 4 provided with truncated pyramidal or frusto-pyramidal hunches 5a mounted on its upper and lower portions to provide a greater end area than the central sectional area and to also provide flat end surfaces. The hunches 5a and 5b are preferably made of a material which does not emit sound in situ when it is pressurized, whose rigidity can be made substantially the same as that of the sample body, and which is capable of being held in close contact with the sample body and permits ready manufacture. A suitable example is a mixture of an epoxy resin and cement, since in this case the rigidity can be varied to a certain extent. These hunches 5a and 5b are provided from the following grounds. The sound which is the subject of measurement is produced from an intermediate portion 4a of the rock sample 4, and it is necessary to prevent generation of sound from the rest of the sample body as much as possible. When the rock sample is pressurized in direct contact with the loading plates, great stress concentration results at the ends of the sample body, and sound waves are also produced due to causes such as wear at the contact surfaces due to deformation of solid.

The hunches 5a and 5b serve to prevent generation of this noise.

The measuring system has the following construction. AE (acoustic emission) transducers 6a, 6b and 6c, such as a ceramic piezo-electric element of 100 KHz resonace type, are provided on the side of the upper and lower loading plates 2a and 2b and at the central portion of the rock sample 4. The outputs of the transducers are led through preamplifiers 7a, 7b and 7c, filters 8a, 8b, and 8c and main amplifiers 9a, 9b and 9c to respective discriminators 10a, 10b and 10c. The discriminators serve to selectively pass signals above a constant detection level so as to prevent introduction of noise. The signals obtained from the transducers 6a and 6b provided on the side of the loading plates 2a and 2b are supplied to a time difference measurement circuit 11, which judges whether or not the detected signal is based upon a sound produced from the interior of the rock and provides as a result of this judgement a gate signal for controlling a gate circuit 12. More particularly, in the time difference measurement circuit 11 the arrival time difference ($\Delta t$) is derived from the phase difference between the waveforms of the two input signals, and the gate circuit 12 is opened only at the time of generation of a signal from the central portion 4a of the rock sample. Meanwhile, the output signal from the transducer 6c provided on the rock sample 4 is coupled through the discriminator 10c to a delay circuit 13, and after a constant delay time, that is, a time required for on-off operating the gate circuit 12 by the gate signal produced from the measurement circuit 11 through determination in the time difference measurement circuit 11 as to whether the detected signal is due to a sound produced from the interior of the rock, it is supplied to the gate circuit 12.

As has been mentioned earlier, since the hunches 3a and 3b are provided at the opposite ends of the sample 3, the generation of noise waves at the opposite ends at the time of loading can be prevented to a considerable extent. However, the noise generation cannot be completely prevented, and introduction of sound waves from other than the sample body 4 such as environmental noise is also possible. The time difference measurement circuit 11 and gate circuit 12 serve to permit only the signal based upon the acoustic emission from the central portion 4a of the rock sample to be picked up so as to improve the precision of measurement. Thus, so long as the gate circuit 12 is opened by the gate signal, the output of the delay circuit 13 is fed through the gate circuit 12 to a emission rate measuring device 14, a counting device 15 and a position determining device 16, and at the same time the time difference signal from the time difference measurement circuit 11 (i.e., locational information) is coupled to the location determining device 16 for data processing.

The emission rate measuring device 14 serves to determine the number of acoustic emissions per unit time so as to obtain the frequency of acoustic emission. The counting device 15 serves to count the number of emissions of sound in during the course of time. In either devices, recording may be directly made by means of a pen recorder while making the measurement or, alternatively, the measured data may be temporarily memorized in a memory device for subsequently drawing a plot by providing the memorized information from the memory. The location determining device 16 has a circuit for counting the deteched signals for individual sections of acoustic emission in the interior of the sample according to the time difference signal, and the results of counting are adapted to be displayed. The data obtained in this way is displayed as a graph showing the relation between the present sections of a rock sample and the number of acoustic emissions from the individual sections and can be utilized for evaluating the reliability of the entire results of the measurement. Where many acoustics, namely sounds, are produced in the vicinity of the end of the sample, the data of measurement cannot be said to provide fairly high reliability.

The results of measurement actually made by this apparatus will now be mentioned. Hunches of a mixture material consisting of an epoxy resin and cement (in a weight ratio of 1:2) were secured to the opposite ends of a rock sample (25 mm $\times$ 25 mm $\times$ 75 mm), and its opposite ends were secured by bonding to respective loading plates. The load on the rock sample which was set in the loading device in this way was gradually increased at a loading speed of 2 mm/min. The electric signals from the individual AE transducers 6a, 6b and 6c were subjected to respective controlled counting processes through the associated circuits. The relation of the number of acoustic emissions with respect to the time elapsed was as shown by broken line in FIG. 3. In the plot showing the relation between the number of emissions of sound obtained from the actual measurement values of the same drawing and the time elapsed, the point of inflection, which is illustrated at "A" in FIG. 3, is clearly noted. The corresponding load is about 0.46 $t$ as derived from the plot of relation between the simultaneously recorded load and the time elapsed (solid plot). This means that this load of about 0.46 $t$ (73.6 kg/cm$^2$) can be thought to show the value of the hysteretic maximum stress in the sample.

Thus, by making the above measurement a number of times with respect to the afore-mentioned three directions to determine the component of hysteretic maximum stress in each directon, it is possible to estimate the three-dimensional stress state of the ground.

Since the invention is based on the above construction, there is no need to bury a strain gauge or like measuring instrument in the ground or to bore a large diameter hole or undertake other comparatively large-scale projects or complicated measurements. It is only necessary to sample rocks in definite positions and directions and subsequently make comparatively simple measurements and analysis of those rocks. Besides, since the site operation is very simple and requires only a short period of time, efficient and economical estimation of the ground pressure can be obtained. Further, according to the invention it is possible to carry out estimation of the magnitude and direction of the ground pressure in fragile ground or rocky ground in the neighborhood of a dislocation; this has been difficult with the conventional over-coring method.

Although the present invention has been described with reference to a preferred embodiment thereof, many modifications and alterations may be made within the spirit of the present invention.

What is claimed is:

1. A method of estimating ground pressure comprising the steps of:
    removing at least one sample rock specimen from the ground location where the ground pressure is to be determined;
    applying a load externally to said rock specimen, and continuously increasing said applied load over a given period of time;

counting the number of acoustic emissions produced from the interior of said rock specimen to which the load is applied during said given period of time;

determining the relationship between the number of acoustic emissions and the time period of measurement and determining the point of inflection of said acoustic emissions during said time period; and comparing the time of said point of inflection with the time of the load applied and determining the load applied at the time of inflection, whereby the hysteretic maximum stress of said rock specimen is determined.

2. A method as claimed in claim 1, further comprising:

affixing a hunch having a section area broader than said rock specimen to each end of said sample before said load is applied; and applying said load against said hunches.

3. A method as claimed in claim 2, wherein said hunch is comprised of a mixture of epoxy resin and cement.

4. A method as claimed in claim 2, wherein a load means is provided for applying said load to said hunches and said hunches have smooth surfaces in contact with said load means.

5. A method as claimed in claim 1, wherein:

a plurality of said sample rock specimens are removed from the desired ground location, each of said specimens being taken with respect to a different direction; and a load is applied to each of said rock specimens and said hysteretic maximum stress of each rock is determined, whereby the stress components of the ground location in the directions represented by each of said rock specimens is determined.

* * * * *